US012797050B2

(12) United States Patent
Malanowska-Stega et al.

(10) Patent No.: US 12,797,050 B2
(45) Date of Patent: Nov. 17, 2026

(54) BRUSH BIOPSY DEVICE, KIT AND METHOD

(71) Applicant: Techmed Ventures, LLC, New York, NY (US)

(72) Inventors: Zanetta Malanowska-Stega, Southampton, NY (US); Damian Stega, Southampton, NY (US)

(73) Assignee: Techmed Ventures, LLC, New York, NY (US)

( * ) Notice: Subject to any disclaimer, the term of this patent is extended or adjusted under 35 U.S.C. 154(b) by 476 days.

(21) Appl. No.: 17/844,685

(22) Filed: Jun. 20, 2022

(65) Prior Publication Data

US 2023/0022536 A1 Jan. 26, 2023

Related U.S. Application Data

(63) Continuation of application No. 15/838,153, filed on Dec. 11, 2017, now Pat. No. 11,364,020.

(60) Provisional application No. 62/432,278, filed on Dec. 9, 2016.

(51) Int. Cl.
*A61B 10/02* (2006.01)
*A61B 10/04* (2006.01)

(52) U.S. Cl.
CPC .......... *A61B 10/02* (2013.01); *A61B 10/0283* (2013.01); *A61B 10/0291* (2013.01); *A61B 10/04* (2013.01); *A61B 2010/0208* (2013.01); *A61B 2010/0216* (2013.01); *A61B 2010/0225* (2013.01)

(58) Field of Classification Search
CPC . A61B 10/02; A61B 10/0283; A61B 10/0291; A61B 10/04; A61B 2010/0208; A61B 2010/0216; A61B 2010/0225
USPC .......................................................... 600/569
See application file for complete search history.

(56) References Cited

U.S. PATENT DOCUMENTS 3,777,743 A * 12/1973 Binard ............... A61B 10/0291 606/119
3,995,618 A * 12/1976 Kingsley ............ A61B 10/0291 600/572
4,227,537 A * 10/1980 Suciu ................. A61B 10/0291 606/162
4,662,381 A * 5/1987 Inaba ................. A61B 10/0291 600/569
8,348,856 B1 * 1/2013 Malanowska-Stega ..................... A61M 25/09 600/565
9,044,213 B1 * 6/2015 Lonky ................ A61B 10/0291
2007/0173736 A1 * 7/2007 Feuer ..................... A61B 17/42 600/572
2012/0289858 A1 * 11/2012 Ouyang ............ A61B 1/00101 600/562

(Continued)

*Primary Examiner* — Chanel J Yoon
*Assistant Examiner* — Chanel J Jhin
(74) *Attorney, Agent, or Firm* — Hoffberg & Associates; Steven M. Hoffberg

(57) ABSTRACT

A biopsy device, comprising a flexible coaxial structure, comprising a wire within a sheath, the wire being adapted to be displaced with respect to the sheath along the coaxial axis by a force applied at a proximal end; a disruptor, at a distal end of the obturator, adapted to disrupt a tissue surface to free cells therefrom, having a first position covered within the sheath and a second position freely extending beyond the sheath; an element, on an exterior of the sheath, configured to limit a depth of insertion of the sheath into a body orifice.

20 Claims, 6 Drawing Sheets

(56) References Cited

U.S. PATENT DOCUMENTS

2015/0088032 A1 * 3/2015 Lee-Sepsick ...... A61B 10/0291
600/570

* cited by examiner

Fig, 2A (Prior Art)

BRUSH BIOPSY DEVICE, KIT AND METHOD

CROSS REFERENCE TO RELATED APPLICATIONS

The present application is a Continuation of U.S. patent application Ser. No. 15/838,153 filed Dec. 11, 2017, now U.S. Pat. No. 11,364,020, issued Jun. 21, 2022, which is a Non-provisional, and claims benefit of priority from U.S. Provisional Patent Application No. 62/432,278, filed Dec. 9, 2017, the entirety of which is expressly incorporated herein by reference.

FIELD OF THE INVENTION

The present invention provides a system and method for performing a biopsy of the uterus. More particularly, it is a device that disrupts and samples cells from the endometrium, and simultaneously takes a sample with an abrasive brush and an aspirate.

BACKGROUND OF THE INVENTION

The present technology represents improvements over U.S. Pat. Nos. 9,351,712, 8,920,336, 8,517,956, and 8,348,856, each of which are incorporated herein by reference in their entirety. Those patents, in turn, represent an improvement over the Cook Medical Tao Brush™ I.U.M.C. Endometrial Sampler, and the Pipelle® endometrial biopsy device (See, Sierecki A R, Gudipudi D K, Montemarano N, Del Priore G., "Comparison of endometrial aspiration biopsy techniques: specimen adequacy." J Reprod Med. 53(10):760-4, 2008 October), expressly incorporated herein by reference.

As shown in FIGS. 1A and 1B, the Tao Brush™ has a bead at the tip, to reduce trauma when the brush reaches the fundus of the uterus. FIG. 1A shows the brush extended from the sheath, while FIG. 1B shows the brush retracted. Proximal to the brush, on the guidewire, is an inner sleeve provided to center the wire, but this does not provide an interference fit, and does not draw a vacuum when the guidewire is retracted. The sample taken by the Tao Brush™ represents the cells swept or abraded from the endometrium, by the bristles. See also, U.S. Pat. Nos. 4,227,537, 3,877,464; 9,078,642; 5,916,175; 5,954,670; 6,059,735; 6,610,005; 7,767,448; 8,827,923; 8,439,847; 8,251,918; 7,749,173; 5,546,265; 3,881,464; 4,108,162; 8,968,213; 8,323,211; D658,388; 5,713,369; 5,546,265; 4,235,244; 4,754,764; 4,763,670; 4,966,162; 5,146,928; 5,253,652; 4,662,381; 5,217,024; 5,279,307; 6,336,905; each of which is expressly incorporated herein by reference in its entirety.

FIGS. 2A and 2B show a Tao Brush™, with the handle at the opposite end from the brush visible.

FIGS. 3A-3D show the use of the Tao Brush™. The manufacturer (Cook Medical) provides the following instructions for use:

1. Position screw-cap test tube containing 8 ml of CytoRich® Brush Cytology Preservative (AutoCyte, Inc., Elon College, NC) in a test-tube rack at the site of the procedure.
2. Place patient in lithotomy position.
3. Retract the brush sampler completely into the outer sheath. (FIG. 2)
4. Gently insert the device to the level of the fundus. (FIG. 3A)

5. Pull back the outer sheath all the way to the handle. Amply rotate the brush sampler. (FIG. 3B)

Two methods are suggested:

1) Rotate brush sampler in a clockwise manner until reference mark on the handle indicates completion of a 360° turn, then rotate counterclockwise the (opposite direction) until the reference mark on the handle indicates completion of a 360° turn;

2) Rotate the brush sampler in only one direction by completing 4 or 5 360° rotations. NOTE: Reference mark on handle indicates completion of a 360° rotation.

6. In order to trap endometrial material in situ, push the outer sheath over the brush to the tip and remove the device. (FIG. 3C). The normal endometrial cavity is in a collapsed state, so the brush will have direct contact with the entire endometrial surface.
7. Immediately immerse the device into 8 ml of CytoRich® Brush Cytology Preservative.
8. Retract the sheath to expose the brush to preservative solution.
9. Hold the sheath firmly and move the brush in and out of the sheath to clean it of adherent cells and tissue. (FIG. 3C) NOTE: Collections are stable in preservative for periods of up to several weeks.
10. Remove the brush assembly from the test-tube, replace the screw cap, and submit the tube to the laboratory for processing.

To Obtain Uncontaminated Endometrial Cultures

1. After insertion of a sterile, nonlubricated vaginal speculum, swab the ectocervix and the endocervical canal with povidone iodine solution. NOTE: Insert the swab about 1.5 cm into the endocervical canal to ensure adequate swabbing of the endocervix with the povidone.
2. Insert the brush into the endometrial cavity following steps 3-6 from the section preceding these instructions. The reference mark on the handle indicates completion of a 3600 turn.
3. Remove sampler.
4. Wipe the rounded tip of the brush with 95% alcohol gauze.
5. Pull back the sheath. Prepare morphologic evaluation (if required) by preparing a direct smear on a sterile glass slide and spray-fix immediately.
6. For culture studies, place the brush into sterile Stuarts Transportation Medium and agitate for 5 seconds FIGS. 4A and 4B show a Pipelle® biopsy tool, which aspirates a sample into a sheath, as shown in FIGS. 5A-5C, but does not have an exposed brush.

FIGS. 6-7 show the design according to U.S. Pat. Nos. 9,351,712, 8,920,336, 8,517,956, and 8,348,856, expressly incorporated herein by reference, which improve the Tao Brush™ design by implementing an aspiration biopsy in addition to an abrasive tissue sampling biopsy. This is achieved by providing an interference fitting plunger proximal to the biopsy brush, which draws in a fluid sample from the uterus as the brush is withdrawn into the sheath.

However, according to the Tao Brush™ design and that of U.S. Pat. Nos. 9,351,712, 8,920,336, 8,517,956, and 8,348,856, the brush is inserted either an arbitrary or estimated distance, or until resistance is encountered by the tip of the brush pushing against the fundus of the uterus, which risks unnecessary tissue damage, and in some cases, complications.

U.S. Pat. Nos. 9,351,712, 8,920,336, 8,517,956, and 8,348,856 discuss an intrauterine biopsy sampling device having a narrow cylindrical tube with a guidewire and biopsy sampling device at the end at the end of the guidewire, similar to a Cook Medical (Bloomington, IN) Tao Brush™ I.U.M.C. Endometrial Sampler, modified such that disposed within the sheath, is a piston-like structure which, when the wire is withdrawn through the sheath, draws a vacuum and sucks fluid surrounding the guidewire into the sheath. A vacuum biopsy sampling device, such as the known Pipelle® endometrial suction curette produces a vacuum and draws it into the sheath by a similar principle, but lacks the brush or other biopsy sampling device at its distal end.

The device is a 1-3 mm diameter by 30-40 cm long coaxial "straw" 1 that can easily pass into the uterus endometrial cavity with little or no discomfort. It is malleable but rigid enough to apply sufficient force to pass through the cervix. In the center of the outer sheath, which is an impermeable tube, a thinner inner insert 2 can be extended beyond the end of the tube 3 into the uterus. Proximal from the biopsy brush is a suction element 4, which draws liquid into the sheath when the guidewire is withdrawn. The inner obturator disrupts the uterus to loosen and collect a biopsy sample of the uterus. The tissue sampling device includes a spirally twisted flexible wire with opposed proximal and distal ends. Also included is a plastic tube covering a significant portion of the wire to provide additional rigidity without making the overall brush stiff.

Along the distal end portion of the wire is a brush that includes bristles that were used for collecting a tissue sample. The bristles are fixed within the spirally twisted wire near the distal end and are tapered from smaller to larger towards the distal end of the wire. Tapering of the bristles from the distal end of the device allows for more global tissue collection of the endometrium because of the shape of the endometrial cavity. An atraumatic bulb is located on the extreme distal end of the twisted wire. The plastic tube and twisted wire are contained within a sheath of shorter length than the twisted wire, such that the sheath can be moved along the plastic tube to the atraumatic bulb on the distal end of the twisted wire, thereby covering the brush during insertion and removal after tissue collection.

Before insertion, the sheath can be moved into position over the distal end of the twisted wire to protect the brush during insertion. Having the brush covered during insertion also increases comfort for the patient and protects the brush from collecting tissue from unintended areas. The sheath is moved back toward the proximal end of the twisted wire after the device has been inserted to the proper collection depth, exposing the brush and allowing for collection of a tissue sample. The sheath may be moved to completely uncover the brush or may be moved in gradients to uncover portions of the brush. This allows the practitioner to adjust the effective collection area of the brush based on the anatomy of the patient.

The plastic tube covering the wire is scored in centimeter gradations along the plastic tube with markings indicating the exact length of the brush inserted into the uterus, starting from the distal tip of the brush to the proximal end of the plastic tube. This allows the clinician to know how deeply the brush is inserted into the uterus. The sheath is approximately the same length as the plastic tube and in position to cover the brush bristles prior to insertion. The sheath may be formed of a clear material such that the gradations on the plastic tube may be viewed through the sheath. The ability to measure insertion depth increases the certainty that the tissue sample collected is from the correct area. After a tissue sample is collected from the proper area, while the tissue sampling device remains inserted, the sheath can be moved back along the distal end of the twisted wire to cover the brush bristles before removing the brush. This allows for the tissue sample to be protected on the brush within the sheath during removal.

Additionally, the gradations along the flexible tube allow the practitioner to measure the length of bristles exposed. As the practitioner pulls the sheath from its insertion position towards the handle, the further the sheath is pulled the more bristles are exposed. The gradations (ruler) provide a visual confirmation of this measurement and allow the practitioner to be precise in exposing only a certain length of the brush bristles. This measurement allows the practitioner to have better control of where the tissue is sampled and allows the practitioner to adjust the length of brush based on patient specific parameters; such as uterine size measured during previous tests or inferred based on patient history. Control of brush exposure increases sampling precision and patient comfort.

Simultaneously with withdrawal of the inner obturator back into the narrow cylindrical tube, the device creates a weak suction to collect the disrupted sample into the outer tube. The entire apparatus is then withdrawn from the uterus and the sample is collected by reversing the process outside the body.

Combining two or more biopsy methods into one device, eliminates pain, discomfort, and inconvenience, e.g., a second procedure to obtain an adequate and accurate specimen. The multiple methods of specimen collection, e.g., disruption by physical means, and suction, used together, allows a gentler application of the individual methods, e.g. a gentle disruption and gentle suction applied simultaneously can replace a vigorous disruption, e.g. D&C, and a powerful suction. The combination of multiple gentler methods in one device is safer and more effective than any method alone.

See (each of which is expressly incorporated here by reference in its entirety):

Borja J M, Galindo P A, Gomez E, Feo F. Contact dermatitis due to povidone-iodine: allergic or irritant?. J Investig Allergol Clin Immunol 2003; 13(2):131-2.

Dijkhuizen F P, Mol B W, Brolmann H A, Heintz A P. The accuracy of endometrial sampling in the diagnosis of the patients with endometrial carcinoma and hyperplasia: a meta-analysis. Cancer 2000; 89(8):1765-72.

Feldman S, Berkowitz R S, Tosteson A N. Cost-effectiveness of strategies to evaluate postmenopausal bleeding. Obstet Gynecol 1993; 81(6):968-75.

Ferry J, Farnsworth A, Webster M, Wren B. The efficacy of the pipelle endometrial biopsy in detecting endometrial carcinoma. Aust N Z J Obstet Gynecol 1993; 33:1-76.

Grimes D A. Diagnostic dilation and curettage: A reappraisal. Am J Obstet Gynecol 1982; 142:1-6.

Guido R S, Kanbour-Shakir A, Rulin M, Christopherson W A. Pipelle endometrial sampling: sensitivity in the detection of endometrial cancer. J Reprod Med 1995; 40:553-5.

Huang G S, Gebb J S, Einstein M H, et al. Accuracy of preoperative endometrial sampling for the detection of high-grade endometrial tumors. Am J Obstet Gynecol 2007; 196:243.e1-243.e5.

Kozuka T. Patch testing to exclude allergic contact dermatitis caused by povidone-iodine. Dermatology 2002; 204 Suppl 1:96-8.

McCluggage W G. My approach to the interpretation of endometrial biopsies and curettings. J Clin Pathol. 2006; 59:801-12.

Naim N M, Mahdy Z A, Ahmad S, Razi Z R M. The Vabra aspirator versus the pipelle device for outpatient endometrial sampling. Aust N Z J Obstet Gynecol 2007; 47(2):132-6.

Ong S, Duffy T, Lenehan P, Murphy J. Endometrial pipelle biopsy compared to conventional dilatation and curettage. Ir J Med Sci 1997; 166:47-9.

Phillips V, McCluggage W G. Results of a questionnaire regarding criteria for adequacy of endometrial biopsies. J Clin Pathol. 2005; 58:417-9.

Ries L A G, Melbert D, Krapcho M, Mariotto A, Miller B A, Feuer E J, Clegg L, Homer M J, Howlader N, Eisner M P, Reichman M, Edwards B K (eds). SEER Cancer Statistics Review, 1975-2004, National Cancer Institute. Bethesda, MD, seer.cancer.gov/csr/1975_2004/, based on November 2006 SEER data submission, posted to the SEER web site, 2007.

Stovall T G, Photopulos G J, Poston W M, Ling F W, Sandles L G. Pipelle endometrial sampling in patients with known endometrial carcinoma. Obstet Gynecol 1991; 77:954-6.

Tahir M M, Bigrigg M A, Browning J J, Brookes S T, Smith P A. A randomized controlled trial comparing transvaginal ultrasound, outpatient hysteroscopy and endometrial biopsy with inpatient hysteroscopy and curettage. Br J Obstet Gynecol 1999; 106(12):1259-64.

Van den Bosch T, Vandendael A, Wranz P A, Lombard C J. Endopap-versus Pipelle-sampling in the diagnosis of postmenopausal endometrial disease. Eur J Obstet Gynecol Reprod Biol 1996; 64:91-4.

Yang G C, Wan L S, Del Priore G. Factors influencing the detection of uterine cancer by suction curettage and endometrial brushing. J Reprod Med 2002; 47:1005-10.

SUMMARY OF THE INVENTION

A preferred embodiment of the present invention provides a narrow cylindrical tube with a guidewire and biopsy sampling device at the end, similar to a Cook Medical (Bloomington, IN) Tao Brush™ I.U.M.C. Endometrial Sampler, modified such that surrounding the cylindrical tube, a cervical stop is provided that limits insertion of the tube to a fixed distance past the external os of the uterus.

This feature may be combined with a suction device to draw a liquid sample in to the lumen of the narrow cylindrical tube, per U.S. Pat. Nos. 9,351,712, 8,920,336, 8,517,956, and 8,348,856.

The device is intended to collect tissue samples from the lining of the uterus (endometrium). The device has a brush at the distal end of the catheter. The brush is intended to gently sample the endometrium. The proximal end of the device has a handle for ease of physician handling. The device has a relatively rigid, outer sheath, that can be move along the length of the device (with respect to the handle), to cover or expose the brush at the distal end.

The device has a skirt stopper around the distal end of the outer sheath. The skirt is intended to locate the device in relation to the cervix, and may be fixed in position or manually slidable along the outer sheath (with a sufficiently tight fit to remain axially fixed in position after placement, such that when abutting the cervix, manipulation of the guidewire and the sheath will not reposition the skirt stopper). A series of axial markings are preferably provided to allow quantitative alignment of the skirt stopper along the sheath. The skirt stopper is preferably made of an elastomer with rounded edges, such as rubber, silicone, or plastic, having sufficient elasticity to provide the desired characteristics and avoid unintended traumatic injury.

The device is intended to be advanced into the patient with the brush covered by the outer sheath until the skirt encounters the cervix and can advance no further. After the skirt is stopped against the cervix, the brush is advanced past the end of the sheath by moving the guidewire with respect to the sheath, to expose the brush inside the uterus, to allow tissue sampling.

The device also has an O-ring secured to the main shaft of the catheter. The outer sheath and O-ring create a seal against each other, and create suction (vacuum) at the distal end of the catheter for securing tissue samples when the guidewire and brush are withdrawn into the sheath.

The device is removed from the patient with the brush covered by the outer sheath. An atraumatic bulb may be provided at the end of the brush, which can seal against the distal end of the sheath when the guidewire is withdrawn into the sheath. A stop may be provided to limit withdrawal of the guidewire into the sheath. For example, a toroidal or cylindrical member attached in fixed position inside the sheath may interfere with the O-ring, and thus limit retraction.

The device preferably sterile, and intended for single-use only.

In accordance with another embodiment of the invention, a multiple sample biopsy device is provided, capable of obtaining and segregating a plurality of biopsy samples taken in a single session. In accordance with this embodiment, the biopsy instrument is placed at an anatomical orifice, such as a cervical os or anus. Advantageously, a protrusion provides a positional reference with respect to the outer portion of the orifice, similar to the aforementioned skirt. This protrusion may be part of the design, or an added element to achieve the desired depth-of-insertion reference function.

The biopsy device according to this embodiment provides a plurality of biopsy sampling tools, which may each be the same or different, e.g., an endocervical sampler, an endometrial sampler, a punch sampler, and an endometrial sampler with suction. Each tool is provided as a device inside a sheath, such as a 1.5-4 mm tube, which is operable by a guidewire to extend the tool sampling head beyond the end of the sheath, twist with respect to the sheath, and retract the tool sampling head back within the sheath.

In addition to providing control over advancing the biopsy tool with respect to the sheath, each sheath is controllable to be selectively inserted into the orifice, and advance into the organ with the biopsy tool retracted into the sheath, and to be removed from the organ with the biopsy tool retracted into the sheath.

In some cases, the sheath itself may be articulable or angularly guidable to direct the biopsy tool to a desired region. The articulable sheath may be a single axis, i.e., a curvature of the end of the sheath, typically as a result of a tension on a tensile element such as cable, guidewire or filament attached to the wall of the sheath. By controlling the angle of curvature, and the rotational angle of the sheath with respect to the organ, a reasonable range of control is provided.

Similarly, a punch, or snare, or encapsulating biopsy device may also be controlled by a tension, which may be a wire or polymer filament. Thus, the case of a single guidewire with a single degree of freedom (advance/retract) is a simplest case, and additional controls and degrees of freedom may be provided.

In some cases, "blind" sampling may be accomplished, for example within a short canal, or at a distal portion of the organ with respect to the orifice.

In other cases, e.g., within a lumen of a larger organ, some imaging guidance is preferred. Therefore, the device may be used with an endoscope, and/or include an endoscopic camera, such as a 1-3 mm endoscopic camera. Typically, such devices rely on fiber optics from the tip to the imager, for both illumination and imaging. However, according to one embodiment of the technology, the imager circuit and lens are present at the tip of the scope, which in turn is disposed proximate to the end of the biopsy sampling device, to provide direct and real-time imaging of the biopsy procedure.

For example, On Semiconductor provides various suitable devices, such as the MT9V115 1/13" VGA, OV6922 1/18" 1/4 VGA imager, and OVM6946 1/18" 400×400 imager, which may be included as part of a subminiature module that transmits the image as a data stream over an electrical interconnection (or wirelessly). The imager is typically provided with a field of view facing the biopsy tool, with a set of LEDs, or LED illuminated fibers, illuminating the field. While the camera is not required in all modes of operation, i.e., all sampling procedures, if provided, it may remain inserted into the orifice throughout the procedure. The camera may be present near the end of the sheath and advanced with the respective sheath of the biopsy tool into the organ during the procedure.

Advantageously, the video signal from the imager may be carried using the guidewire(s) which control the biopsy tool as electrical power and/or signal carriers. Note that the operating voltage is typically low, e.g., <3.3V, so a dangerous condition for the patient would not be present in case of electrical leakage. However, the power carrying members may be insulated to further reduce risk and enhance signal integrity. A wireless transmission may also be provided, for example to a nearby wireless receiver, avoiding the need for wired transmission. In that case, the device may have a self-contained battery, or receive operating power over a conductor which advantageously may include the guidewire. Since the preferred guidewire is multi-stranded, power and ground, and even signal, may be transmitted if the strands are mutually insulated. There is no compelling reason why a guidewire needs to be uninsulated, so this permits enhanced use of an existing structure, at low added cost and complexity.

The biopsy device according to this embodiment provides a barrel cartridge with the various biopsy tools in angularly displaced positions. One way to selectively activate certain tools is to provide the barrel with a single active position, in which the manipulator controlled by the user provides functional control over a single one of the plurality of biopsy tips, e.g., extension and retraction of the sheath, and extension, retraction and rotation of the guidewire. As discussed above, a function for articulation of the sheath by tension on another actuation filament may also be provided. The remaining biopsy tools in the barrel may remain restrained in their undeployed positions, e.g., clamped in position.

Because the barrel has a larger diameter than the sheath, the barrel is maintained outside of the orifice, and a mechanism for engaging and disengaging each respective biopsy tool is also outside the orifice, which, for example, may rotate into position to release one tool while locking the others in retracted position. Thus, a relatively large barrel, e.g., 8-20 mm, may be provided with 2-12 biopsy tools in reserve. The end of the barrel mechanism advantageously serves as the skirt, to limit insertion distance of the sheath into the organ, and provide a well-defined positional reference.

According to a first embodiment, each biopsy tool in the device is separate, with no changeover in control. Thus, for a biopsy device with four deployable biopsy tools, there are four separate sheaths with respective guidewires extending from the cartridge. This permits a physician to select the appropriate biopsy tools for a respective procedure, from generic or custom designs. The unused tools remain outside of the organ, while an active tool is in use. In some cases, multiple tools may be advanced into the organ, for example where an endoscope is provided as one of the available tools, and not linked to a particular or single biopsy tool.

On the other hand, in a second embodiment, a mechanism may be provided to mechanically separately engage the sheath, guidewire, and articulation wire for each separate biopsy tool, with a single control system extending from the cartridge. For example, a multi-way clamp, bayonet socket, quick-release, or magnetic mechanism may be provided to individually engage the respective biopsy tool in the active position. The cartridge is typically round, and centered at the orifice during the procedure, so that the non-deployed biopsy devices are eccentric within the cartridge when not in use. As they are brought into the active position, such as by rotation of a lockout/clamp control, and centering, the controls for that respective biopsy tool are also connected and made active. The camera may also be attached to the active biopsy tool at this time. Alternately, the camera is inserted in advance of the biopsy tool, and is separately positioned from the biopsy tools.

In some cases, an electrical mechanism may be provided in the cartridge, for example to latch the mechanical controls, extend the sheath to a desire depth of insertion, rotate the brush, and retract the sheath and/or biopsy brush into the sheath. Typically, the extension of the biopsy brush and axial manipulation are user controlled, and not automated, though a completely automated biopsy is possible.

It is preferred that each biopsy tool have a mechanical limiter to control and constrain the movements within a predetermined range, wherein the predetermined range may differ for the various biopsy tools depending on their intended use of application. Advantageously, axial control limits are referenced to the exterior surface surrounding the orifice of insertion, and the end of the barrel, a ring or protrusion surrounding the barrel, used to maintain this position reference without slipping into the orifice.

For example, the endocervical brush will typically have the sheath extend 0-2 cm past the orifice, and an endometrial brush will typically have the sheath extend 2-10 cm past the cervix, into the uterus, and a brush biopsy tool will extend 1-3 cm beyond the end of the sheath. The endocervical and endometrial brushes may be provided with or without suction, which may be provided by mechanical action of a plunger as the guidewire controlling the brush is withdrawn into the sheath, or by a vacuum provided through the sheath from the cartridge or beyond.

A puncher or cup biopsy tool are typically used under visual observation with the video imager, and may be less mechanically constrained in this circumstance, since the user is presumed to have control over the device during use.

Therefore, the present design permits multiple biopsies to be taken in a single session, from different regions of the organ, and maintained segregated from each other. From a patient perspective, this is advantageous, because the sampling procedure is facilitated, and the combined time and economic burden will typically be less than if separate biopsy tools are employed. Further, compatibility with a single imager used for a plurality of biopsy procedures is also efficient. Finally, in the case of a cartridge that disconnects from a standard handle, the cartridge provides an efficient way to organize and label the samples from a single patient, and makes pathological examination of the various samples from the same patient and same organ more efficient. Finally, because each sample is accurately depth labelled with respect to the orifice, clinically important information is obtained, as compared to traditional biopsy tools which do not provide an accurate depth reference. It is noted that a memory card, such as a micro-SD card, may be associated with the cartridge, which includes video and/or manipulation history information for each biopsy tool, which is automatically recorded and maintained, and which may be readily passed to the pathologist or made part of the patient's record.

It is therefore an object to provide a tissue sampling device, comprising: a flexible sheath having at least a distal portion configured to maintain an internal vacuum; a skirt stopper configured to maintain the sheath at a fixed insertion depth through the cervix within the uterus; and a displaceable structure within the sheath, to form a coaxial structure; the displaceable structure having a first end extending from a proximal end of the sheath and second end configured to, in a first state, extend from a distal end of the sheath, and in a second state, to be retracted into the distal end of the sheath; the second end of the displaceable structure having a cellular sampling structure, preceded by a suction element; and the coaxial structure being configured such that a tension on the first end of the displaceable structure at the proximal end of the sheath results in a retraction of the displaceable structure from the first state to the second state, to generate the suction to cause a displacement of media external to the sheath into the sheath distal to the piston.

The displaceable structure may terminate at the second end in an atraumatic bulb.

The cellular sampling structure may comprise a brush.

The brush may comprise a plurality of bristles extending radially from the displaceable structure. The brush may have a cross section which tapers with respect distance from the second end. The brush may have a helical cross sectional profile.

The coaxial structure may be configured for insertion to a predetermined depth into the cervical os of a uterus of a human, to retrieve an endometrial biopsy sample, and to be withdrawn from the cervical os of the uterus.

The coaxial structure may be further configured to be: inserted into the cervical os with the displaceable structure in the second state to a predetermined depth; extended into the first state with the cellular sampling structure within the uterus; manipulated by a user by movement of the first end of the displaceable structure to dislodge cells within the uterus; retracted into the second state within the uterus, to cause the vacuum to withdraw a liquid sample surrounding the cellular sampling structure in to the distal end of the sheath; and retracted from the cervical os with the displaceable structure in the second state.

The displaceable structure may comprise a spirally twisted flexible guidewire.

The sheath may have an outer diameter of between 1 and 3 mm and a length between 20 and 50 cm.

It is also an object to provide a tissue sampling method, comprising: providing a coaxial structure, comprising a flexible sheath having at least a distal portion configured to maintain an internal vacuum, a skirt around the flexible sheath, configured to limit an insertion depth of the flexible sheath into a human cervix; and a displaceable structure within the sheath, to form a coaxial structure, the displaceable structure having a first end extending from a proximal end of the sheath and second end configured to, in a first state, extend from a distal end of the sheath, and in a second state, to be retracted into the distal end of the sheath, and the second end of the displaceable structure having a cellular sampling structure, preceded by a piston; and applying a tension on the first end of the displaceable structure at the proximal end of the sheath to case retraction of the displaceable structure from the first state to the second state, generating the vacuum.

The coaxial structure may be configured for insertion into the cervical os of uterus of a human to the predetermined insertion depth, to retrieve an endometrial biopsy sample, and to be withdrawn from the cervical os of the uterus.

The method may, further comprise: inserting the distal portion of the coaxial structure into the cervical os of a uterus, with the displaceable structure in the second state to the predetermined depth; extending the distal portion of the coaxial structure into the first state with the cellular sampling structure within the uterus; manipulating the first end of the displaceable structure to dislodge cells within the uterus; retracting the coaxial structure into the second state within the uterus, to cause the vacuum to withdraw a liquid sample surrounding the cellular sampling structure in to the distal end of the sheath; and retracting the distal portion of the coaxial structure from the cervical os with the displaceable structure in the second state.

The cellular sampling structure may comprise a brush having a plurality of radially extending bristles from the displaceable structure and terminating in an atraumatic bulb.

The displaceable structure may comprise a spirally twisted flexible guidewire, further comprising twisting the guidewire to rotate the cellular sampling structure.

It is a still further object to provide a flexible coaxial biopsy device, comprising: a tubular sheath having a wall configured to maintain an internal vacuum with respect to an exterior of the tubular sheath; a flanged element on an outer surface of the tubular sheath, configured to limit a depth of insertion of the tubular sheath into a cervix; a displaceable wire within the tubular sheath; and a cellular sampling device configured to disrupt a surface of a tissue, mounted on the displaceable structure distal to the element, configured to protrude from a distal end of the tubular sheath when the displaceable element is disposed in a first state, and to be contained within the distal end of the tubular sheath when the displaceable element is disposed in a second state.

The cellular sampling device may comprise a plurality of bristles extending outwards from the displaceable wire, terminating at the distal end in an atraumatic bulb.

The device may be configured for insertion into the cervical os of a uterus of a human to the predetermined depth, to retrieve an endometrial biopsy sample from inside the uterus, and to be withdrawn from the cervical os of the uterus after the endometrial biopsy sample is obtained.

The device may be further configured to be: inserted into the cervical os with the displaceable wire in the second state to the predetermined depth; extended into the first state with the cellular sampling device within the uterus; manipulated by movement of the first end of the displaceable wire to dislodge endometrial cells; retracted into the second state within the uterus, to draw the vacuum to withdraw a liquid sample surrounding the cellular sampling device in to the distal end of the tubular sheath; and retracted from the cervical os with the displaceable wire in the second state.

The device may further comprise an element that creates a negative pressure within the tubular sheath when the displaceable wire is withdrawn into the tubular sheath.

The biopsy brush described above may also be revised for use as an anal biopsy brush, and an endometrial biopsy brush and anal biopsy brush may be provided together as a kit, optionally alone with a vial of preservative solution (for a single brush), or a plurality of vials of preservative for a kit. The kit is preferably a sterile package, which may be double wrapped, containing the biopsy brush or bushes, a vial or vials of preservative, and optionally an acceptable lubricant for cytological sampling, and optionally a disposable sterile sheet or drape.

The anal biopsy brush differs from an intrauterine biopsy brush in that it will be shorter, since the working distance between the physician or caregiver and patient orifice is less. The, for intrauterine use, the sheath is typically 20-25 cm long, with a 4 cm long brush and 2 cm exposed guidewire, such that the wire is 26-31 cm long, past the end of the handle to which it is bound, with a skirt on the sheath about 4 cm from the distal end.

An anal biopsy brush sheath will typically be 8-12 cm long, with the skirt about 4 cm from the distal end. For example, an anal biopsy brush may have a sheath 8 cm long with the skirt located 4 cm from the distal end, having a guidewire 14-18 cm long for sampling in the rectum up to 6 cm past the end of the sheath.

A kit may therefore include a long intrauterine biopsy device having a sheath length of about 20 cm, a short anal biopsy device having a sheath length of about 8 cm, two vials of cytological preservative, a packet of water-based cytologically acceptable lubricant (e.g., Surgilube®, which preferably does not include carbomers), a sterile drape, and package insert labelling instructions (which may be imprinted on the packaging as appropriate). Any lubricant should be applied on the exterior of the sheath, between the skirt or flange and distal tip, with the brush in the retracted position, with care taken to avoid getting lubricant on the end of the sheath or brush.

BRIEF DESCRIPTION OF THE DRAWINGS

FIGS. 1A, 1B, 2A and 2B, show a prior art Tao Brush™ in the extended and retracted state with respect to the sheath, respectively, the inner obturator and disrupting elements, which may be, for example, a brush, tapered helical screw, loop or loop with brush elements, or the like;

DETAILED DESCRIPTION OF THE PREFERRED EMBODIMENTS

Example 1

Figure 1A:
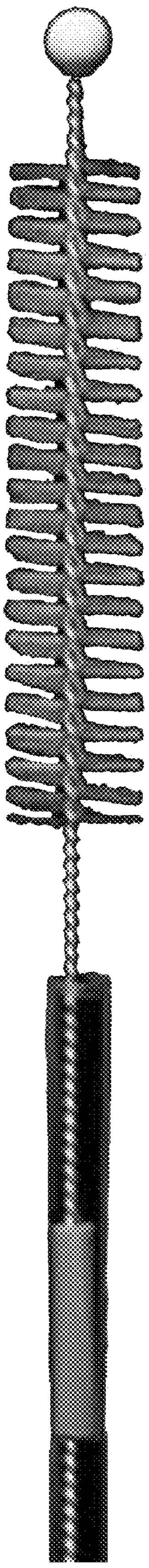
Fig. 1A (Prior Art)
Figure 1B:
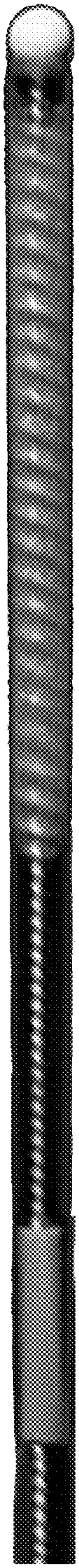
Fig. 1B (Prior Art)
Figure 2B:
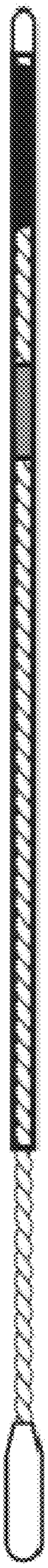
Fig. 2B (Prior Art)
Figure 2B:
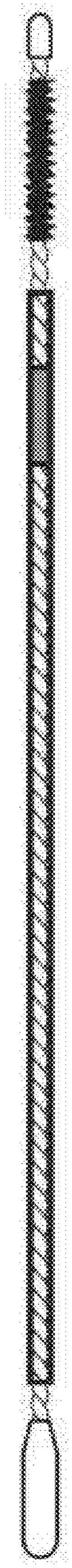
Fig. 2B (Prior Art)
Figure 3C:
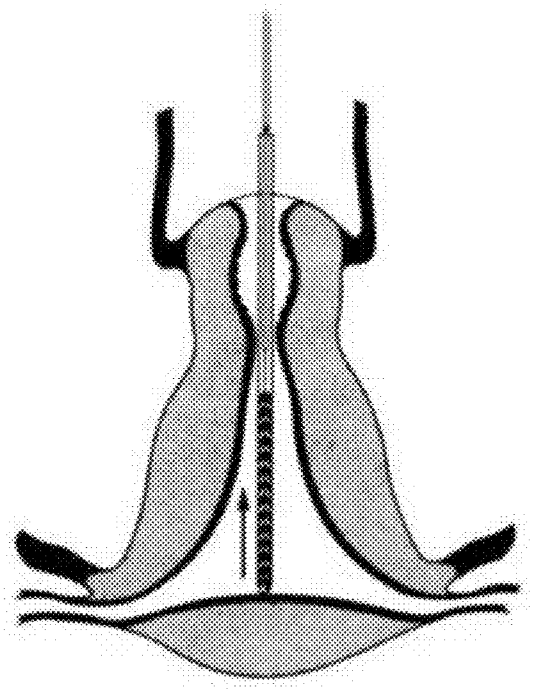
Fig. 3C (Prior Art)
FIGS. 3A-3D show illustrations of use of the Tao Brush™.
Figure 3D:
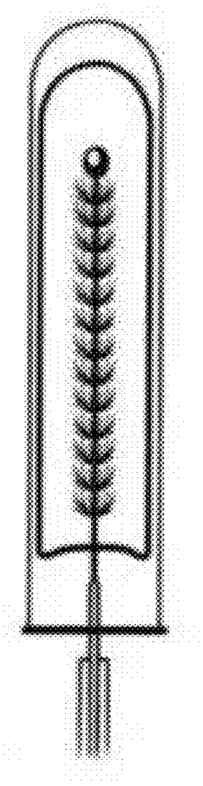
Fig. 3D (Prior Art)
Figure 3A:
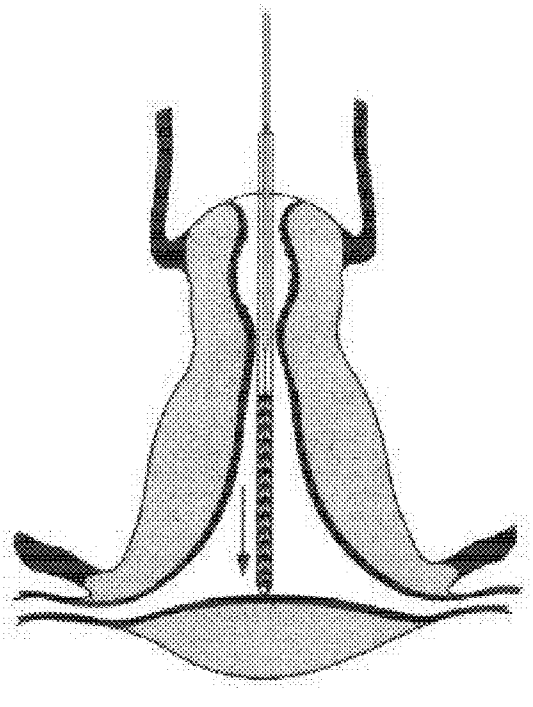
Fig. 3A (Prior Art)
Figure 3B:
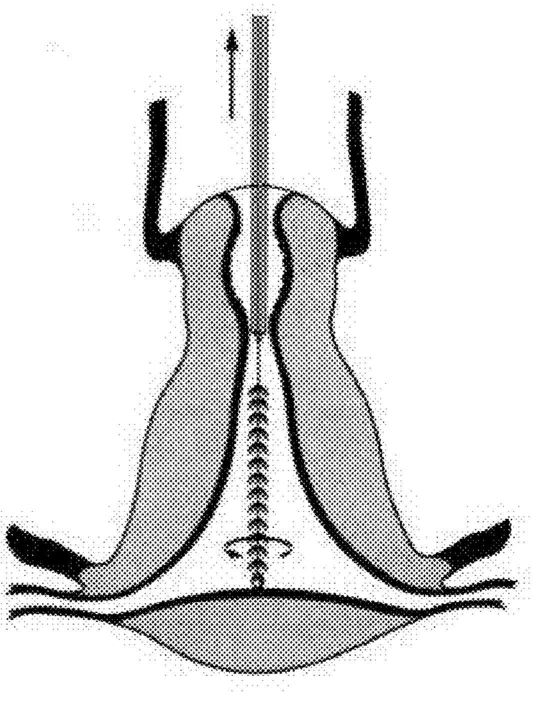
Fig. 3B (Prior Art)
Figure 4A:
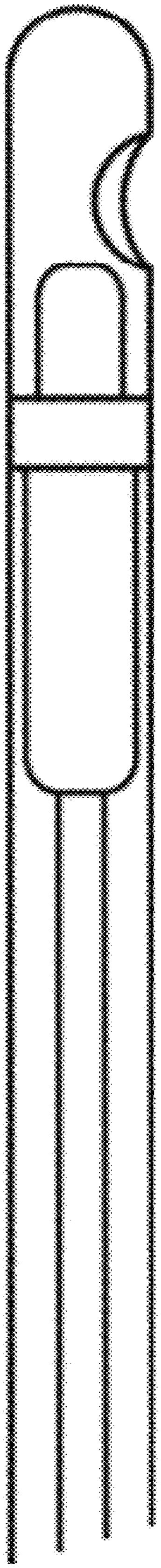
Fig. 4A (Prior Art)
FIGS. 4A and 4B show a Pipelle® endometrial biopsy device of the prior art, in the extended and retracted states, respectively.
Figure 4B:
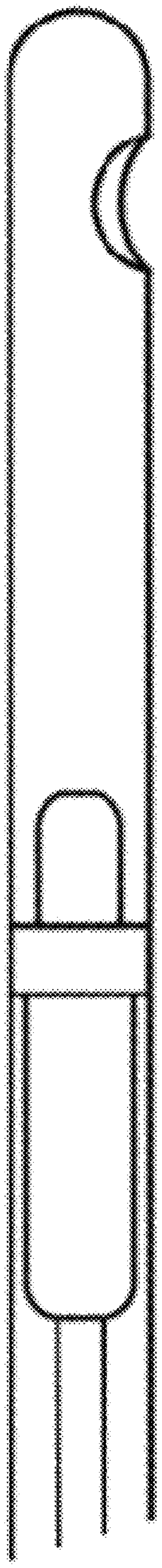
Fig. 4B (Prior Art)
Figure 5C:
Fig. 5C (Prior Art)
FIGS. 5A-5C shows use of Pipelle® device in a biopsy procedure.
Figure 5B:
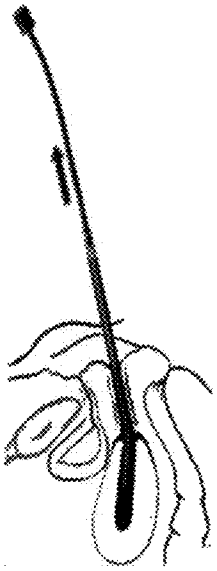
Fig. 5B (Prior Art)
Figure 5A:
Fig. 5A (Prior Art)
Figure 6:
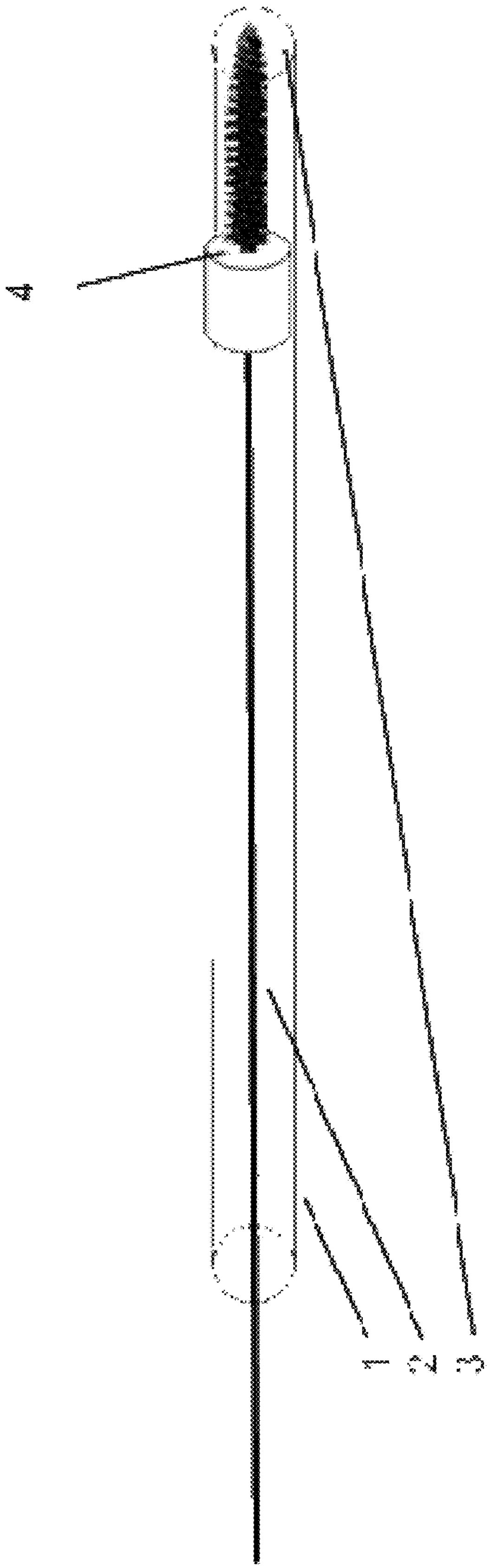
Fig. 6 (Prior Art)
FIGS. 6 and 7 show an improved endometrial biopsy brush with suction, according to U.S. Pat. Nos. 9,351,712, 8,920,336, 8,517,956, and 8,348,856.
Figure 7:
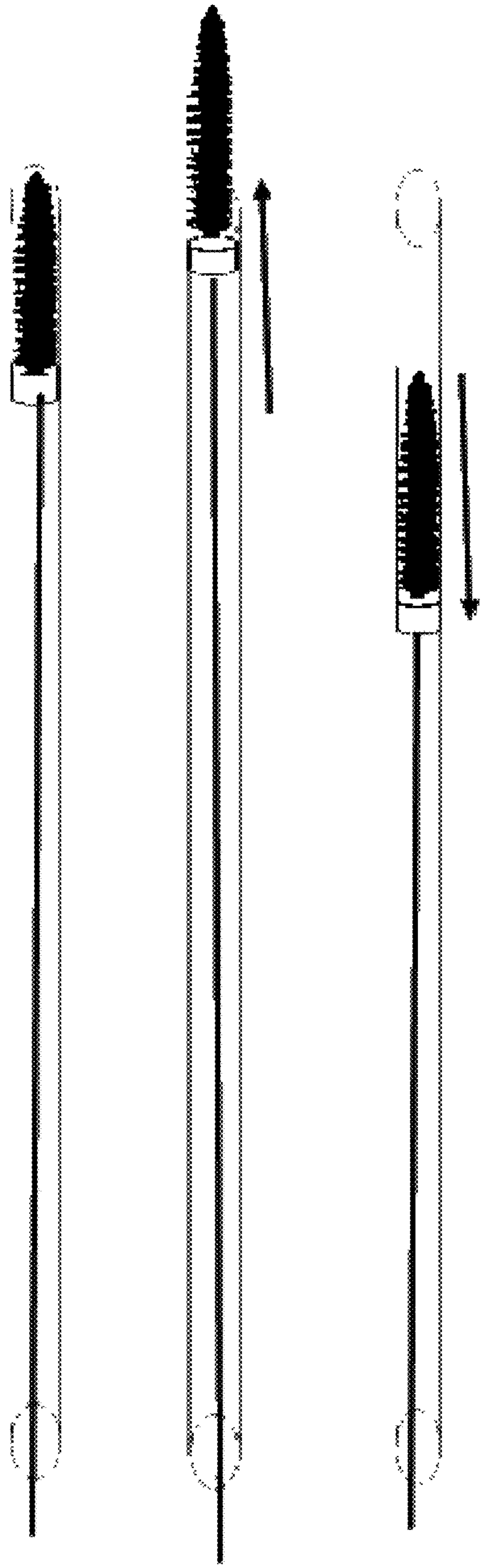
Fig. 7 (Prior Art)
Figure 8:
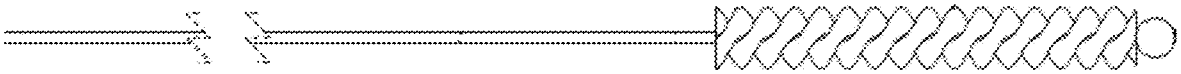
FIG. 8 shows a guidewire and biopsy brush according to the present invention.

A preferred embodiment of the present invention consists of an intrauterine biopsy device having an outer thin-walled tube of approximately 2.25 mm outside diameter and 1.2 mm inside diameter; length is between 20-50 cm, e.g., 22 cm. This tube may be a clear, bendable but self-supporting plastic tube, made e.g., of nylon. The guidewire is preferably a twisted stainless steel wire of approximately 0.1-0.2 mm diameter, having sufficient mechanical properties to convey the forces for extension and retraction of the brush during use. At the distal end of the guidewire is a biopsy brush, shown in FIGS. 8 and 11, tipped with an atraumatic bulb. The brush may be about 4 cm long, and extend about 2 cm past the end of the sheath when extended. The O-ring preferably remains within the sheath over the entire range of travel, to avoid problems re-engaging the end of the sheath. For example, the O-ring (or more generally, plunger attached to the wire) may be, for example, 2-5 mm from the end of the sheath when extended.

An anal biopsy device may also be provided, having an outer thin-walled tube of approximately 2.25 mm outside diameter and 1.2 mm inside diameter; length is between 8-12, e.g., 8 cm. This tube may be a clear, bendable but self-supporting plastic tube, made e.g., of nylon. The guidewire is preferably a twisted stainless steel wire of approximately 0.1-0.2 mm diameter, having sufficient mechanical properties to convey the forces for extension and retraction of the brush during use. At the distal end of the guidewire is a biopsy brush, shown in FIGS. 8 and 11, tipped with an atraumatic bulb. The brush for the anal biopsy device may also be 4 cm long, with the O-ring or plunger 2-5 mm from the end of the sheath when the brush is extended.

The wire may be periodically marked, such as in 1 cm increments, so that the physician or biopsy device operator can estimate the brush insertion with respect to the proximal end of the sheath.

At one end, the one that enters the uterus or anus, the biopsy brush is formed. A tight fitting O-ring around the guidewire, shown in FIG. 11, acts as a piston and creates the suction as the obturator is withdrawn through the outer thin walled tube.

In another embodiment, the O-ring may be disposed about 2.5 cm from the tip, with the brush extending about 1.5 cm from the tip, with 1 cm of bare wire between them.

Figure 9:
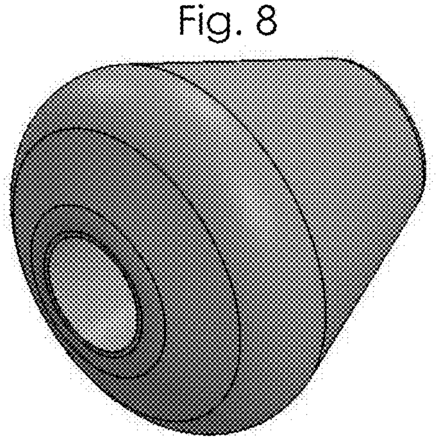
FIG. 9 shows a shirt stopper according to the present invention.
Figure 10:
FIG. 10 shows a narrow sheath with skirt stopper installed according to the present invention.
Figure 11:
FIG. 11 shows a complete biopsy device with manual handle, skirt stopper, sheath, guidewire, brush, and O-ring, according to the present invention.

As shown in FIGS. 9, 10 and 11, a skirt stopper is provided about the exterior of the thin-walled tube, near the distal end, which may be in fixed position or manually slidable. The skirt is approximately 1 cm in diameter, and may be formed of nylon, polyurethane, silicone, neoprene, or other medically acceptable plastic or rubber. Typically, the skirt is fixed in position, and may be glued (e.g., UV activated methyl-methacrylate adhesive) or molded to the sheath in position.

The biopsy device is used as follows:

The brush is retracted completely into the outer sheath.

The sheath is inserted, through the vagina, into the cervix, until the skirt stopper meets the external os of the cervix. The tip of the brush should be displaced from the fundus.

The outer sheath is pulled back until it stops, i.e., abuts the handle. The brush is then rotated by holding the sheath still and turning the handle. For example, the brush may be rotated in a clockwise manner until a reference mark on the handle indicates completion of a 360° turn, and then rotated counterclockwise until the reference mark on the handle indicates completion of a −360° turn. Alternately, the brush may be rotated in only one direction by completing 4 or 5 360° rotations. In some cases, the brush may be repositioned axially, though it should not be withdrawn into the sheath until the sampling is completed.

After sampling with the brush, the guidewire is pulled at the handle, until the sheath hits the stop (e.g., the edge of the handle), thereby suctioning fluid surrounding the tip into the sheath, and then withdrawing the brush into the sheath.

After withdrawal of the device from the vagina, the brush and fluids in the sheath are immersed in a cytology preservative, such as formalin, and the sample is washed from the brush into the preservative by moving the brush in and out of the sheath immersed in the fluid.

The invention may be used, for example, to sample the inside of the uterus to diagnose abnormalities. It can detect or exclude a cancer. It can obtain an adequate tissue sample to determine infertility causes.

The anal brush is similarly employed. Such a biopsy tool typically has a shorter sheath and guidewire than an endocervical brush biopsy tool, because of the easier anatomical access. For example, the sheath may be 10-15 cm long, and the brush may extend 2-6 cm beyond the end of the sheath. As with the endocervical brush biopsy tool described above, a skirt is preferably provided which prevents insertion of the sheath into the anus beyond the sheath, to provide a physical reference distance for insertion. In some cases, the skirt may be repositioned on the sheath, to permit the physician the ability to determine at what depth of insertion the sample should be acquired. Advantageously, the readjustment requires more force than would be available by applying an unconstrained compression of the sheath against the skirt stopper, so that the position is maintained during use, but the stiction force can be overcome when the biopsy tool is external to the body.

Example 2

According to a second embodiment, a multiple sample biopsy device is provided, capable of obtaining and segregating a plurality of biopsy samples taken in a single session. This therefore requires a plurality of biopsy brushes or tools, and a plurality of sheaths in which the tools are extended and retracted.

As discussed above, a depth of insertion positional reference, such as a skirt stopper may be provided. However, where the multiple biopsy tool system has a mechanism maintained outside of the orifice, the diameter of the tool may be sufficiently large to act as the stopper without additional structures.

According to one design, each biopsy tools is separate, including a sheath and guidewire control. A set of biopsy tools are aggregated in an outer tube housing. The tube has a conical internal profile at the distal end, so that a single biopsy tool may be advanced past the end of the housing, into the orifice or canal from which a biopsy is to be taken. In some cases, endoscopic guidance of the biopsy is desired, and in that case, a second sheath which supports the endoscope and lighting may be advanced as well. He endoscope sheath may also inject saline for visualization, though in the case of a brush biopsy, this is disfavored, since the saline will wash away the dislodged cells, and reduce the positional accuracy of sampling. An inert gas, such as $CO_2$ may also be injected through the sheath, in known manner.

For example, the biopsy brush may be provided in a 3 mm tube, with 6 separate brushes provided within a housing. A stop may be provided at the proximal end of each sheath within the housing, to prevent over-withdrawal. Markings may be provided on each sheath, to inform the physician about the depth of insertion. In some cases, the physician may intend gradated sampling at a series of depths in the orifice, and advantageously, each respective sheath may have a stopper which limits its depth of insertion, and provides the physician with haptic feedback when that depth is achieved. This stopper may be a simple O-ring or clamp, which is adjusted by the physician for each biopsy sampling tool, before the procedure. The guidewire for each sampling tool may also have depth limits. Of course, the retracted position with the biopsy tool fully withdrawn into the sheath represents one extreme, and a clamp or limit may be provided on the manipulation end to control how far the guidewire may be extended beyond the end of the sheath.

In this first design, each biopsy brush may be of known type, with the optional addition of the insertion and retraction limiters, and indeed, the housing for arranging a multiple biopsy sample session may itself be provided independent of the biopsy brushes.

In general, the housing avoids the need for a separate skirt stopper, though the housing may terminate in a skirt stopper.

Example 3

According to a second design of the multiple sample biopsy device, a single manipulator extends from a housing, which itself contains a plurality of biopsy tools.

As discussed above, a depth of insertion positional reference, such as a skirt stopper may be provided. However, where the multiple biopsy tool system has a mechanism maintained outside of the orifice, the diameter of the tool may be sufficiently large to act as the stopper without additional structures.

Thus, a selectively engageable coupling is provided between a single guidewire and the various tools. The coupling thus links the guidewire, that extends to a physician manipulation interface, such as a grasping element, a handle, or a pivotal mechanism, to the individual guidewire for each tool. Advantageously, the plurality of tools are provided in a rotating barrel, which serves as the housing. Each biopsy tool, when engaged with the manipulation guidewire, can be advanced with its respective sheath an insertion distance, and then the biopsy head advanced beyond the sheath, and twisted or otherwise manipulated to obtain a biopsy sample. The biopsy head is then withdrawn back into the sheath, the sheath with biopsy head covered then withdrawn back into the cartridge, and the barrel twisted so another biopsy tool may then be engaged.

Therefore, the coupling is a coaxial coupling, which separately links and controls the sheath and the guidewire within each respective sheath. For example, within the cartridge, the end of the sheath may terminate in a steel ring, which is magnetically permeable. Thus, a magnetic coupling can be used to connect and disconnect the sheaths. Further, the inactive biopsy tools may also be held in place by another magnet, which is typically an electromagnet, or a permanent magnet with an electromagnetic release. The guidewire may be selectively connected to the external manipulation guidewire with a spring-loaded clamp. As the barrel is turned, the spring-loaded clamp releases, and re-engages as it reaches the next detent position with the next biopsy tool aligned with the spring clamp. Within the barrel, the guidewire from the biopsy tool extends beyond the proximal end of the respective sheath.

The barrel is typically at least as long as the desired depth of insertion of the sheath into the patient. Thus, if it is desired to have a 12 cm depth of insertion, the barrel mechanism may be 13-16 cm long.

Figure 12:
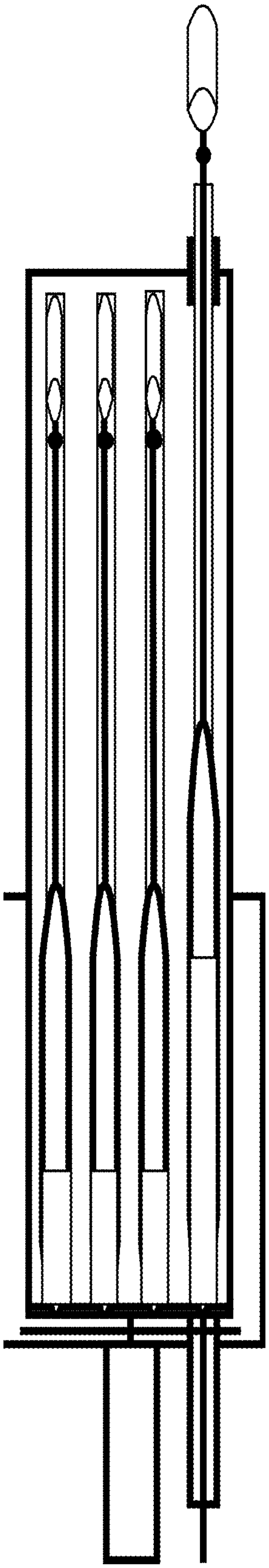
FIG. 12 shows an arrangement of an independently controllable, biopsy multiple sample, biopsy device showing four similar biopsy sampling tools.
Figure 13:
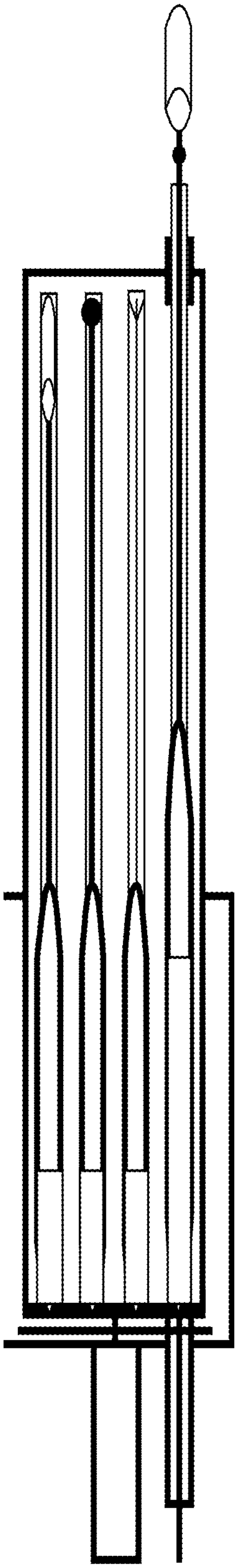
FIG. 13 shows an arrangement of an independently controllable, biopsy multiple sample, biopsy device showing four different biopsy sampling tools.

As shown in FIG. 12, a plurality of similar brushes are provided in a cartridge. In FIG. 13 a plurality of different brushes are provided in the cartridge. The cartridge has an exit port for the engaged biopsy tool. Each brush has its own associated sheath, which may be independently advanced into the patient, depending on which tool is engaged. A mechanism at the proximal end of the housing controls the selection of the barrel position by an angle of rotation, the latching of the sheath of the respective active tool to the tool advancement control, the clamping of the guidewire of the respective active tool to the guidewire control for manipulation by the physician, and in some cases, other controls, such as deflection angle of the sheath.

Figure 14:
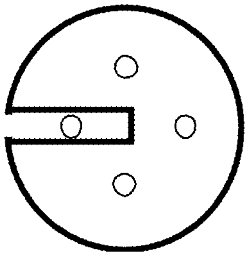
FIG. 14 shows a detail of a selector which permits manipulation of a single biopsy sampling tool in a barrel cartridge.

FIG. 14 shows an end view of a portion of the mechanism in the barrel, wherein one guidewire is free to be manipulated by the physician, while access for manipulation of the other guidewires is locked out.

FIG. 12 shows a bulb provided just proximal to each sampling brush, which is provided to draw a sampling vacuum when the respective brush is withdrawn back into the sheath.

In FIG. 13, only one biopsy tool has such a feature. The biopsy sampling tools, may be, for example, an endocervical sampler, an endometrial sampler, a punch sampler, and an endometrial sampler with suction.

In some cases, the sheath itself may be articulable or angularly guidable to direct the biopsy tool to a desired region. The articulable sheath may be a single axis, i.e., a curvature of the end of the sheath, typically as a result of a tension on a tensile element such as cable, guidewire or filament attached to the wall of the sheath, not shown in in the figures. By controlling the angle of curvature, and the rotational angle of the sheath with respect to the organ, a reasonable range of control is provided. Similarly, a punch, or snare, or encapsulating biopsy device may also be controlled by a tension, which may be a wire or polymer filament. Thus, the case of a single guidewire with a single degree of freedom (advance/retract) is a simplest case, and additional controls and degrees of freedom may be provided. The controls for these tools may also be selectively engaged through a mechanism, or be provided individually to the user.

An endoscopic imager (not shown in the figures) may be provided, preferably as a feature of the housing, so that it may be used with various biopsy tools within the housing. For example, a 1-3 mm endoscopic camera with fiber optic lighting, may be provided, e.g., the On Semiconductor OVM6946 1/18" 400×400 imager.

What is claimed is:

1. An endometrial tissue biopsy device, comprising:

a coaxial structure comprising an impermeable tube having a diameter of between 1 mm to 3 mm surrounding a wire displaceable within the impermeable tube, the coaxial structure being configured for insertion through a cervical os into a uterus;

a brush on an end of the wire, having a first position in which the brush is contained within the impermeable tube, and a second position in which the brush extends beyond an end of the impermeable tube, the brush being displaceable from the first position to the second position by compression of the wire in the impermeable tube, displaceable from the second position to the first position by tension of the wire in the impermeable tube, and rotatable about a wire axis in the second position by a twisting of the wire, the brush being configured to obtain a cellular endometrial biopsy sample;

a piston surrounding the wire, the piston being disposed behind the brush with respect to the end of the impermeable tube, and the piston being configured to draw a vacuum at the end of the impermeable tube when the brush is displaced from the second position to the first position;

an atraumatic tip at a distal end of the brush, configured to block the end of the impermeable tube when the brush is in the first position; and a stop surrounding an exterior wall of the impermeable tube, configured to maintain the impermeable tube at an insertion depth within the uterus during the compression, tension and twisting of the wire, wherein the stop comprises a flanged elastomer disk configured to abut the cervical os and the impermeable tube comprises a plastic tube, and the flanged elastomer disk is glued to the plastic tube with an ultraviolet (UV) light activated methyl methacrylate adhesive.

2. The endometrial tissue biopsy device according to claim 1, wherein the coaxial structure is configured for insertion through the cervical os to a predetermined insertion depth within the uterus of a human.

3. The endometrial tissue biopsy device according to claim 1, wherein the wire comprises a plurality of spirally-twisted strands, and the brush comprises a plurality of bristles inserted between respective spirally-twisted strands, wherein the bristles have a length longer than an inner diameter of the impermeable tube, and are deflected in the first position.

4. The endometrial tissue biopsy device according to claim 1, wherein the impermeable tube has a length between 20 and 50 cm, and the wire is longer than the tube.

5. The endometrial tissue biopsy device according to claim 1, wherein the stop has a diameter of 1 cm.

6. The endometrial tissue biopsy device according to claim 1, wherein the impermeable tube has a diameter of between 1 mm and 3 mm.

7. The endometrial tissue biopsy device according to claim 1, further comprising:

a second coaxial structure comprising a second impermeable tube surrounding a second wire displaceable within the impermeable tube;

a second brush on an end of the second wire, having a first position of the second brush in which the second brush is contained within the second impermeable tube, and a second position of the second brush in which the second brush extends beyond an end of the second impermeable tube, the second brush being displaceable from the first position of the second brush to the second position of the second brush by compression of the second wire in the second impermeable tube, displaceable from the second position of the second brush to the first position of the second brush by tension of the second wire in the second impermeable tube, and rotatable about a second wire axis in the second position of the second brush by a twisting of the second wire, the second brush being configured to obtain the cellular endometrial biopsy sample from an endometrial tissue lining;

a second piston surrounding the second wire, the second piston being disposed behind the second brush with respect to the end of the second impermeable tube, and the second piston being configured to draw a vacuum at the end of the second impermeable tube when the second brush is displaced from the second position of the second brush to the first position of the second brush;

a second atraumatic tip at a distal end of the second brush, configured to block the end of the second impermeable tube when the second brush is in the first position of the second brush;

wherein the stop surrounds the first impermeable tube and the second impermeable tube.

8. The endometrial tissue biopsy device according to claim 7, further comprising a housing, configured to selectively attach one of the first wire and the second wire to a user interface, such that when selectively attached, tension and compression are passed from the user interface to the first wire or second wire to transition between the first position of the second brush and the second position of the second brush, and when detached, tension and compression are not passed from the user interface to the first wire or second wire.

9. The endometrial tissue biopsy device according to claim 1, further comprising an electronic camera attached near the end of the impermeable tube, configured to communicate images of a biopsy procedure when the brush is in the second position.

10. The endometrial tissue biopsy device according to claim 9, further comprising a light emitting diode illuminator configured to illuminate an endometrial tissue.

11. An endometrial tissue biopsy method, comprising:

providing:

a coaxial structure having a diameter of between 1 mm and 3 mm, comprising an impermeable tube surrounding a wire displaceable within the impermeable tube;

a brush on an end of the wire, the brush being configured to obtain a cellular biopsy sample from an endometrium;

a piston surrounding the wire, the piston being disposed behind the brush with respect to an end of the impermeable tube;

an atraumatic bulb at a distal end of the brush, configured to block the end of the impermeable tube when the brush is in a first position in which the brush is contained within the impermeable tube; and a stop surrounding an exterior wall of the impermeable tube;

inserting the coaxial structure through a cervical os into a human cervix, with the end of the impermeable tube through the cervical os within a uterus;

extending the brush from the first position, to a second position in which the brush extends beyond the end of the impermeable tube by compression of the wire in the impermeable tube;

twisting the wire to thereby rotate the brush while in the second position;

withdrawing the brush from the second position to the first position by tension of the wire in the impermeable tube;

drawing a vacuum within the end of the impermeable tube by displacement of the piston into the impermeable tube by the tension of the wire, to thereby draw a liquid endometrial tissue sample into the impermeable tube;

maintaining the impermeable tube at an insertion depth within the uterus during the compression, tension and twisting of the wire; and maintaining the impermeable tube at the insertion depth within the uterus with the stop in a vagina abutting the cervical os, wherein the stop comprises a flanged elastomer disk, the impermeable tube comprises a plastic tube, and the flanged elastomer disk is glued to the plastic tube with an ultraviolet (UV) activated methyl methacrylate adhesive.

12. The endometrial tissue biopsy method according to claim 11, wherein the flanged elastomer disk is formed of polyurethane.

13. The endometrial tissue biopsy method according to claim 11, wherein the wire comprises a plurality of spirally-twisted strands, and the brush comprises a plurality of bristles inserted between respective spirally-twisted strands, wherein the bristles have a length longer than an inner diameter of the impermeable tube, further comprising deflecting the bristles upon withdrawal of the brush from the second position to the first position.

14. The endometrial tissue biopsy method according to claim 11, wherein the flanged elastomer disk has a diameter of 1 cm.

15. The endometrial tissue biopsy method according to claim 11, wherein the flanged elastomer disk is formed of silicone.

16. The endometrial tissue biopsy method according to claim 11, further comprising:

providing:

a second coaxial structure comprising a second impermeable tube surrounding a second wire displaceable within the second impermeable tube;

a second brush on an end of the second wire configured to obtain the cellular biopsy sample from the endometrium;

a second piston surrounding the second wire, the second piston being the piston being disposed behind the second brush with respect to an end of the second impermeable tube;

a second atraumatic bulb at a distal end of the second brush, configured to block the end of the second impermeable tube when the second brush is in a first position of the second brush in which the second brush is contained within the second impermeable tube;

wherein the stop surrounds the first impermeable tube and the second impermeable tube;

inserting the second coaxial structure through the cervical os into the human cervix, with the end of the second impermeable tube past the human cervix within the uterus;

extending the second brush from the first position of the second brush, to a second position of the second brush in which the second brush extends beyond the end of the second impermeable tube by compression of the second wire in the second impermeable tube;

twisting the second wire to thereby rotate the second brush while in the second position of the second brush to obtain the cellular biopsy sample from the endometrium;

withdrawing the second brush from the second position of the second brush to the first position of the second brush by tension of the second wire in the second impermeable tube;

drawing a vacuum within the end of the second impermeable tube by displacement of the second piston into the second impermeable tube by the tension of the second wire, to thereby draw the liquid endometrial tissue sample into the second impermeable tube; and maintaining the second impermeable tube at a second insertion depth within the uterus with the stop in the vagina abutting the cervical os.

17. The endometrial tissue biopsy method according to claim 16, further comprising:

providing a housing, configured to selectively attach one of the first wire and the second wire to a user interface, such that when selectively attached, tension and compression are passed from the user interface to the first wire or second wire to transition between the first position of the second brush and the second position of the second brush, and when detached, tension and compression are not passed from the user interface to the first wire or second wire;

selectively attaching the first wire to the user interface to transmit tension and compression from the user interface to the first wire and not the second wire; and selectively attaching the second wire to the user interface to transmit tension and compression from the user interface to the second wire and not the first wire.

18. An endometrial tissue biopsy device, comprising:

a coaxial structure configured for insertion through a human cervix into a human uterus, comprising:

an impermeable tube surrounding a wire displaceable within the impermeable tube;

a brush on an end of the wire, having a first position in which the brush is contained within the impermeable tube, and a second position in which the brush extends beyond an end of the impermeable tube, the brush being displaceable from the first position to the second position by compression of the wire in the impermeable tube, displaceable from the second position to the first position by tension of the wire in the impermeable tube, and rotatable about a wire axis in the second position by a twisting of the wire, the brush being configured to obtain a cellular endometrial biopsy sample;

a piston surrounding the wire, the piston being disposed behind the brush with respect to the end of the impermeable tube, configured to draw a vacuum at the end of the impermeable tube when the brush is displaced from the second position to the first position; and an atraumatic bulb at a distal end of the brush, configured to block the end of the impermeable tube when the brush is in the first position; and an annular element fixed in position on an outer wall of the impermeable tube, configured to abut the human cervix and prevent entry of the annular element into the human cervix, while the coaxial structure is guided through the human cervix into the human uterus, wherein the annular element comprises a flanged elastomer disk, the impermeable tube comprises a plastic tube, and the flanged elastomer disk is adhered to the plastic tube with an ultraviolet (UV) light activated methyl methacrylate adhesive.

19. The endometrial tissue biopsy device according to claim 18, wherein the impermeable tube has a diameter of between 1 and 3 mm, and the annular element comprises a 1 cm diameter skirt stopper.

20. The endometrial tissue biopsy device according to claim 18, wherein the wire comprises a twisted stainless steel wire having a diameter of between 0.1 mm and 0.2 mm.

* * * * *